United States Patent [19]

Novick et al.

[11] Patent Number: 4,897,264

[45] Date of Patent: Jan. 30, 1990

[54] HUMAN GAMMA INTERFERON-SPECIFIC RECEPTOR PROTEIN, ANTIBODY AGAINST SAID PROTEIN, METHODS FOR OBTAINING SAID PROTEIN AND SAID ANTIBODY AND COMPOSITIONS CONTAINING SAID PROTEIN AND ANTIBODY

[75] Inventors: Daniela Novick; Patricia Orchansky; Dina Fischer, all of Rehovot; Menachem Rubinstein, Givat Shmuel, all of Israel

[73] Assignee: Yeda Research and Development Co., Ltd., Rehovot, Israel

[21] Appl. No.: 30,640

[22] Filed: Mar. 27, 1987

[30] Foreign Application Priority Data

Apr. 8, 1986 [IL] Israel ........................................ 78444

[51] Int. Cl.⁴ ...................... A61K 39/00; A61K 45/02
[52] U.S. Cl. .................................... 424/85.5; 435/183
[58] Field of Search ........................ 424/85.5; 435/183

[56] References Cited

U.S. PATENT DOCUMENTS

| | | | |
|---|---|---|---|
| 4,617,378 | 10/1986 | Rubinstein | 424/85.5 |
| 4,650,674 | 3/1987 | Aggarwal | 425/85.5 |
| 4,751,078 | 6/1988 | Nagabhushan | 425/85.5 |

Primary Examiner—Peter D. Rosenberg
Attorney, Agent, or Firm—Browdy & Neimark

[57] ABSTRACT

Analysis of [$^{125}$I]. interferon gamma cross-linked to its receptor on various human cells by SDS-PAGE revealed that there are at least three different types of human interferon gamma receptors. In WISH, HeLa, FS11 and the other tissue cells an Mr 90,000–105,000 receptor was found. In monocytes and in the myeloid cell line KG-1 an Mr 140,000 receptor was found while in Daudi lymphoblastoid cells an Mr 95,000–115,000 receptor was found.

The various receptors were isolated from these cells by extraction followed by affinity chromotography on an immobilized interferon gamma column. The resulting purified preparations retained their original affinity for interferon gamma and were used for immunizing mice and subsequent development of highly specific antibodies.

22 Claims, 6 Drawing Sheets

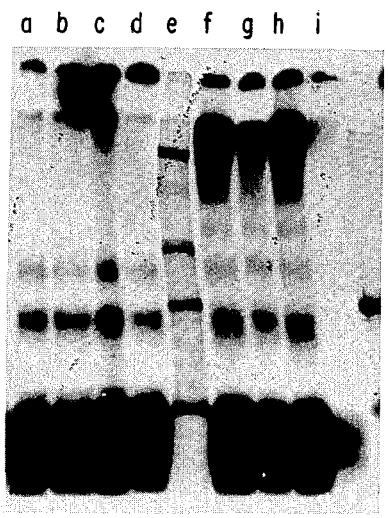

ANALYSIS BY SDS-PAGE (7.5%) AND AUTORADIOGRAPHY OF IMMUNO-PRECIPITATED CROSS-LINKED COMPLEX OF [125I]-IFN-γ AND ITS RECEPTOR. LANE a: LOAD FRACTION; LANE b : EFFLUENT; LANES c &d : WASH FRACTIONS LANE e: MOLECULAR WEIGHT MARKERS FROM TOP TO BOTTOM: MYOSIN: 200,000; PHOSPHORYLASE B: 92,000; BOVINE SERUM ALBUMIN: 69,000; OVALBUMIN: 46,000); LANES f, g & h : ELUTION FRACTIONS; LANE i: ELUTION FRACTION N°6 IMMUNOPRECIPITATED WITH CONTROL SERUM.

*FIG. 6.*

HUMAN GAMMA INTERFERON-SPECIFIC RECEPTOR PROTEIN, ANTIBODY AGAINST SAID PROTEIN, METHODS FOR OBTAINING SAID PROTEIN AND SAID ANTIBODY AND COMPOSITIONS CONTAINING SAID PROTEIN AND ANTIBODY

BACKGROUND OF THE INVENTION

The invention herein concerns antibodies directed against different receptors of interferon gamma on human cells. Such antibodies can block the action of interferon gamma on some cells and not on others, thus leading to selective action of interferon gamma as a pharmaceutical agent or to prevention of the action of endogenous interferon gamma on some cells and not on others.

Interferon gamma is a lymphokine produced by activated T-lymphocytes and exerting many immunoregulatory activities. It is generally known as an immune stimulant because of its ability to activate monocytes and macrophages towards cell killing in vitro (Le et al., 1983, J. Immunol. 131, 2821–2823).

In addition, interferon gamma is a direct inducer of class I and II major histocompatibility complex (MHC) antigens in both immune and non-immune cells (Steeg et al., 1982 J. Exp. Med. 156, 1780; Wallach et al., 1982 Nature 299, 833–836). So far, it is the only known direct inducer of class II MHC antigens and it exerts its effect even at very low concentrations (1–10 pM).

Class II major histocompatibility antigens (HLA-DR in humans) play a major roll in the immune system. These transmembranal proteins are mainly expressed on monocytes, macrophages, B lymphocytes, langerhans cells and thymus epithelial cells. They are absent from most tissue specific cells and from resting T cells. The genes of these proteins show extensive polymorphism which results in a large number of different serotypes.

In general, T-lymphocytes respond to a given antigen only when it is presented on the surface of an "antigen presenting cell" such as monocytes and in combination with class II major histocompatibility antigens such as HLA-DR in humans and Ia in mice. Once this occurs, an antigen specific clonal expansion of T helper cells will take place. These T cells will induce cytotoxic/suppressor T cells on one hand and will "help" B cells to mature and become antibody producing plasma cells. Another important function of HLA-DR is in the interaction of T cells with B cells which is essential for proliferation and maturation of B cells. Further details on the role of HLA-DR are found in immunology textbooks (e.g. *The Immune System* by I. McConnell, A. Munro and M. Waldman, Blackwell Scientific Publications, 1981, Oxford). Thus interferon gamma, plays a central role in the intitiation of the immune response by modulating the level of surface HLA-DR on antigen presenting cells and it plays an important role in augmenting cellular cytotoxicity.

Additional studies have shown that the induction of HLA-DR by interferon gamma is not limited to hematopoietic cells. In fact many types of cells including fibroblasts, endothelial cells, keratinocytes, astrocytes and thyroid follicular cells will express HLA-DR after exposure to low doses of interferon gamma in vitro.

As to the role of HLA-DR in non-hematopoietic cells there is a debate among various investigators. Thus, Mason and Barclay (Immunobiology 168, 167–171, 1984) pointed out that Ia positive cells (Ia is the mouse equivalent of human HLA-DR) are also producing interleukin-1 and therefore can be suitable as antigen presenting cells. They specifically referred to vascular endothelial cells (Hirshberg et al., 1980, J. Exp. Med. 152, 2495), keratinocytes (Luger et al., 1982, J. Immunol. 128, 2147) and astrocytes (Fontana et al., 1982, J. Immunol. 129, 2143). In all of these cases, T cell proliferation which was taken as a measure of immune stimulation was induced by these Ia positive, non-hematopoietic cells. More recently, Bottazzo et al., (Lancet 1983, II, 1115; Immunol. Today 5, 23, 1984) proposed that the expression of HLA-DR on thyroid follicular cells may be involved in the initiation and maintenance of autoimmune dieases of the thyroid gland. Later (Londei et al., Science 228, 85, 1985) they identified T-cell clones which originated from autoimmune thyroid glands and recognized autologous HLA-DR positive thyroid cells. These authors suggested that autoimmune thyrocytes "may act as antigen presenting cells that present their own surface autoantigens". In another study, Fierz et al., (J. Immunol. 134, 3785–3793, 1985) demonstrated that interferon gamma treated astrocytes are Ia positive and that such treatment augments up to four-fold the induction of T-cell proliferation by contact with said astrocytes. These authors state that it is conceivable that "abnormal" induction of Ia antigens on astrocytes by some stimulus is a basis for the development of an autoimmune disease in the central nervous system. While the above studies were performed in vitro, a recent in vivo study was performed by Groenewegen et al., (Nature 316, 361–363, 1985). Using cyclosporin A, a known inhibitor of interferon gamma production, they have demonstrated that class II antigen expression by canine endothelial cells was not constitutive but rather it was interferon gamma dependent. These authors also suggested that class II MHC products (e.g., HLA-DR in humans and Ia in murine cells) of non-hematopoietic cells are involved in immune responses.

The conclusion of the aforesaid studies was mainly circumstantial and based only on cell to cell interaction and T-cell proliferation. However, in none of the cases reported so far, direct cytotoxicity of T-cells against HLA-DR bearing tissue cells or induction of specific autoantibodies was reported. These thoughts were expressed recently by Mowat (Lancet, Aug. 3, 1985, p. 283) who suggested that "enhanced expression of class II MHC antigens in autoimmune disease merely reflects the involvement of effector T-lymphocytes in the tissue pathology" and although he did not dismiss the role of HLA-DR in worsening autodestructive processes, he suggests a careful experimental considersation.

Three unrelated lines of research indicate, in an indirect way, that in fact the situation may even be opposite to what was so far expected, namely, it is possible that interferon gamma actually inhibits immune response by inducing HLA-DR on non-hematopoietic cells. Taramelli et al. (Int. J. Cancer 34, 797–806, 1984) studied the role of HLA-DR on metastatic human melanoma cells in suppressing autologous lymphocyte mediated cytotoxicity and lymphocyte proliferation. Human tumor cells can stiumlate in 60–70% of the cases the proliferation of autologous lymphocytes and their differentiation into tumor specific cytotoxic T-cells. This is effected via production of IL-2. Taramelli et al., found that metastatic melanoma cells (from lymph nodes) can inhibit the IL-2 dependent stimulation of autologous lymphocytes. This inhibition was observed only with HLA-DR positive melanoma cells. Moreover, on treatment of HLA-DR negative cells with interferon gamma they became HLA-DR positive and acquired the suppressive activity. Thus, the induction of HLA-DR on melanoma cells by interferon gamma was circumstantially linked to inhibition of an autologous lymphocyte mediated cytotoxicity. If this phenomenon is not limited to neoplastic cells but rather it occurs in all cells, then the appearance of HLA-DR on tissue cells associated with an autoimmune disease maybe a part of the homeostatic response which inhibits tissue damage by monocytes, killer cells and cytotoxic T-lymphocytes. Indeed, recently it was reported by Biogen Inc., that cancer patients who suffered from rheumatoid arthritis and were given interferon gamma as a potential antineoplastic drug showed signs of improvement in their arthritis. In a preliminary study, 70% of the patients experienced relief from their pain and swelling. These observations may be related to an enhanced expression of HLA-DR on sinovial cells as was demonstrated in vitro.

The best documented role of interferon gamma as a suppressor of cell mediated cytotoxicity is in the field of natural killer (NK) activity. Several studies have demonstrated that while interferon activates NK cells towards killing of target cells it also renders these target cells more resistant to NK (Trincieri and Santoli, 1978, J. Exp. Med. 147, 1314; Hansson et al., 1980, J. Immunol. 125, 2225; Welsh 1981, Antiviral Res., 1, 5; Wallach 1982, J. Interferon Res. 2, 329; Wallach 1983, Cellular Immunol. 75, 390). It appears therefore that interferon gamma may have opposing effects on different cells. Monocytes and NK cells are activated by interferon gamma and became more efficient in their function as cytotoxic cells, while various non-hematopoietic cells which are potential targets for lysis may become NK resistant. Moreover, certain tumor cells (metastatic melanoma, Taramelli et al., Int. J. Cancer 34, 797, 1984; murine leukemia, Ramila and Erb, Nature 304, 442, 1983; glyomas, Gately et al., Acta Neurochirug. 64, 175, 1982; and lyposarcoma, Roth et al., J. Immunol. 130, 303, 1983), have immunosuppressive activity which is possibly linked with the expression of HLA-DR on their surface.

SUMMARY OF THE INVENTION

The invention herein is directed to antibodies developed against the various forms of the interferon gamma receptor which can block the binding of interferon gamma to some cells and not to other cells in a selective manner. The invention is based on the observation that human cells of different tissue bear different receptors for interferon gamma. Since interferon gamma exerts opposite effects on various cells, selective blockage of its receptors on e.g. immune cells can for instance reduce the immunostimulatory effects of interferon gamma while maintaining its ability to interact with non immune cells and render them resistant to the damage caused in autoimmune diseases.

The invention further concerns methods for preparing the purified active form of these receptors and the antibodies directed against them. The invention also concerns pharmaceutical preparations containing the aforesaid antibodies and methods of using same for administration as immuno-regulators for various autoimmune diseases.

BRIEF DESCRIPTION OF THE DRAWINGS

FIG. 6: Analysis by SDS-PAGE (7.5%) and autoradiography of immunoprecipitated cross-linked complex of [$^{125}$I]-IFN-gamma and its receptor. Lane a: Load fraction; lane b: Effluent; lanes c and d: wash fractions; lane e: molecular weight marker from top to bottom; Myosin: 200,000; phosphorylase B: 92,000; bovine serum albumin: 69,000; ovalbumin: 46,000); lanes f, g and h: Elution fractions; lane i: elution fraction No. 6 immunoprecipitated with control serum.

DESCRIPTION OF THE INVENTION

The receptors of interferon gamma on various human cells were identified by cross-linking experiments with radiolabelled interferon gamma. Briefly pure interferon gamma was labelled with [$^{125}$I] according to published procedures. The resulting preparation exhibited intact biological activity. Such labeled interferon was allowed to react with various human cells at 4° C. and the resulting interferon-receptor complexes were covalently cross-linked. The cross-linked complexes were then analyzed by polyacrylamide gel electrophoresis (PAGE) in the presence of Nadodecyl sulfate (SDS) followed by autoradiography. As shown in the examples, human cells of different tissue origin exhibited interferon gamma receptors having different molecular weights, thus indicating that they are structurally different.

The receptors from various cell lines were then purified by affinity chromatography on an immobilized interferon gamma column without loss of their ability to bind interferon gamma. These purified preparations were used for developing antibodies that block selectively the binding of interferon gamma to some cells and not to other cells. The invention is further illustrated by way of Examples.

EXAMPLE 1.

Crosslinking of [$^{125}$I]-IFN-gamma to its receptor in intact cells

Figure 1:
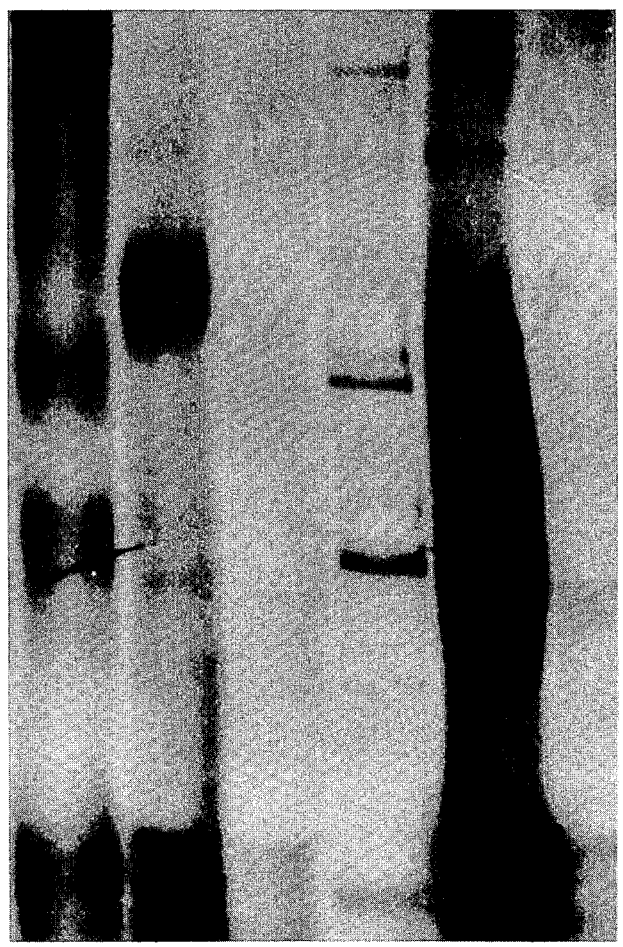
FIG. 1: Binding and crosslinking of [$^{125}$I]-IFN-gamma to receptor on WISH cells and KG-1 cells and competition with unlabeled IFN-gamma. Lane 1: [$^{125}$I]-IFN-gamma crosslinked with itself; lane 2: [$^{125}$I]-IFN-gamma crosslinked to WISH cells; lane 3: [$^{125}$I]-IFN-gamma crosslinked to WISH cells in the presence of 100-fold excess unlabeled IFN-gamma; lane 4: molecular weight markers (from top to bottom: myosin. 200,000; phosphorylase B: 92,000; bovine serum albumin: 69,000; ovalbumin: 46,000); lane 5: [$^{125}$I]-IFN-gamma crosslinked to KG-1 cells; lane 6: [$^{125}$I]-IFN-gamma crosslinked to KG-1 cells in the presence of 100-fold excess unlabeled IFN-gamma.

Cells (1-2×10$^8$ cells, according to the cell type) were incubated with [$^{125}$I]-IFN-gamma with or without excess unlabeled IFN-gamma for 1.5 hrs at 4° C. in PBS containing Ca$^{++}$ and Mg$^{++}$. A non cleavable cross-linking reagent [dissuccinimidyl suberate (DSS)] was added at a final concentration of 0.5-1 mM for 20 min at 4° C. The cells were then washed and resuspended in 50 mM Tris-HCl, 0.1M NaCl, pH 7.5 containing 1.5% Triton X-100 for 1 h at 4° C. with gentle stirring. The preparations were centrifuged at 27,000×g for 20 min. The supernatants were immunoprecipitated with rabbit anit-IFN-gamma serum (prepared by immunizing rabbits with homogenous IFN-gamma) diluted 1:50. After 2 hrs at room temperature a suspension of Protein-A Sepharose was added and left for 1 h at room temperature. The Sepharose beads were then washed, and bound material was dissociated by the addition of SDS-PAGE sample buffer. Analysis of the samples was done by SDS-PAGE (7.5%). FIG. 1 shows the apparent M.Ws of the [$^{125}$I]-IFN-gamma crosslinked to its receptor on WISH and KG-1 cells. For WISH cells (FIG. 1 lane 2) a broad band of M.W. 105,000-130,000 was found. Assuming that the receptor binds one molecule of IFN-gamma (25 kD), the calculated M.W. of the receptor must be 90,000 to 105,000. (KG-1 Myeloid cells (FIG. 1, lane 5) shows a sharp band of M.W. 165,000 giving a receptor of M.W. 140,000-150,000. An addition of a 100-fold excess of unlabeled IFN-gamma prevented the formation of these cross-linked complexes (FIG. 1, lane 3, WISH lane 6, KG-1) indicating the specificity in the binding. Bands with M.Ws lower than 92,000 correspond to IFN-gamma cross-linked with itself as it is shown in FIG. 1, lane 1.

Figure 2:
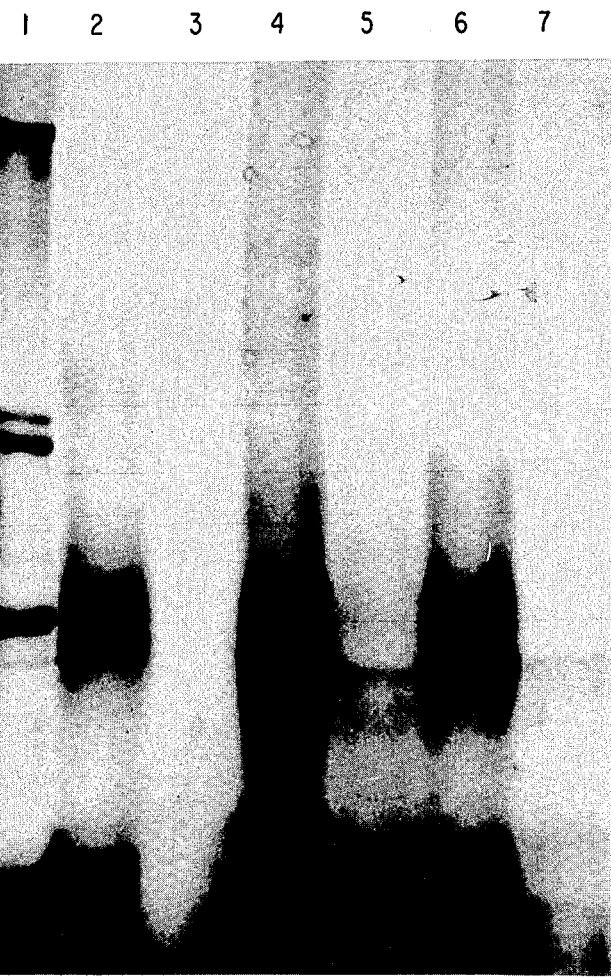
FIG. 2: Binding and crosslinking of [$^{125}$I]-IFN-gamma to receptors and competition with unlabeled IFN-gamma. Lane 1: molecular weight markers: (from top to bottom: Myosin: 200,000; phosphorylase B: 92,000: bovine serum albumin: 69,000; ovalbumin: 46,000); lane 2: [$^{125}$I]-IFN-gamma crosslinked to Wish cells; lane 3: [$^{125}$I]-IFN-gamma crosslinked to WISH cells in the presence of 100-fold excess unlabeled IFN-gamma. lane 4: [$^{125}$I]-IFN-gamma crosslinked to normal peripheral blood monocytes; lane 5; [$^{125}$I]-IFN-gamma crosslinked to normal peripheral blood monocytes in the presence of 100-fold excess unlabeled IFN-gamma. lane 6: [$^{125}$I]-IFN-gamma crosslinked to normal peripheral blood T-lymphocytes; lane 7: [$^{125}$I]-IFN-gamma crosslinked to normal peripheral blood T-lymphocytes in the presence of 100-fold excess unlabeled IFN-gamma.

FIG. 2 shows a similar pattern, [$^{125}$I]-IFN-gamma cross-linked to the receptor in WISH cells appeared to have a M.W. of 105,000-130,000. When [$^{125}$I]-IFN-gamma was cross-linked to the receptor in normal peripheral bloodmonocytes a band of M.W. 165,000 was obtained. This band was identical to the one that was seen in KG-1 cells (myeloidic cell line). Normal peripheral blood T-lymphocytes did not show any detectable band that appeared with M.W. lower than 92,000 correspond to IFN-gamma cross-linked with itself.

Figure 3:
FIG. 3: Binding and crosslinking of [$^{125}$I]-IFN-gamma to receptors and competition with unlabeled IFN-gamma. Lane 1 and 6: Molecular weight markers: (from top to bottom: Myosin: 200,000; phosphorylase B: 92,000; bovine serum albumin: 69,000); lane 2: [$^{125}$I]-IFN-gamma crosslinked to WISH cells; lane 3: [$^{125}$I]-IFN-gamma crosslinked to WISH cells in the presence of 100-fold excess unlabeled-IFN-gamma; lane 4: [$^{125}$I]-IFN-gamma crosslinked to H-229 cells; lane 5: [$^{125}$I]-IFN-gamma crosslinked to H-229 cells in the presence of 100-fold excess unlabeled-IFN-gamma; lane 7: [$^{125}$I]-IFN-gamma crosslinked to MOLT-4 cells; lane 8: [$^{125}$I]-IFN-gamma crosslinked to MOLT-4 cells in the presence of 100-fold excess unlabeled-IFN-gamma; lane 9: [$^{125}$I]-IFN-gamma crosslinked to DAUDI cells; lane 10: [$^{125}$I]-IFN-gamma crosslinked to DAUDI cells in the presence of 100-fold excess unlabeled-IFN-gamma.

FIG. 3 shows the same molecular weight for the receptor on WISH cells as previously shown. Hela H-229 cells (fibroblastic cell line) shows a broad band of 105,000-130,000 for the complex, DAUDI cells (B-lymphoblastoid) shows also a broad band of 120,000-140,000. MOLT-4 (T-cell line) did not show any detectable complex.

EXAMPLE 2

Isolation of IFN-gamma receptors from human WISH cells

Figure 4:
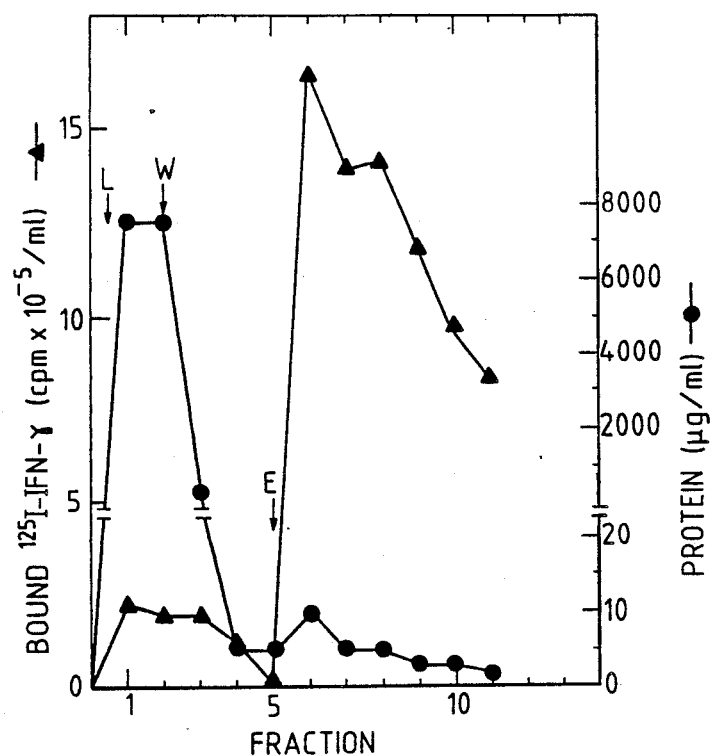
FIG. 4: Elution profile of the IFN-gamma receptor from the affinity column. Each fraction was tested for its ability to bind [$^{125}$I]-IFN-gamma ( —▲— ) and for protein content ( —●— ). L: Load; W: WASH; E: elution fractions. Protein was determined with fluorescamine.

Human WISH cells were grown in minimal essential medium supplemented with 10% foetal bovine serum and glutamine 2 mM. Cells were washed with phosphate buffered saline (PBS). 1-10×10$^{10}$ cells were solubilized in a solubilization buffer (final concentrations: 10 mM Hepes, pH 7.4, 1-2% Triton X-100, 1 mM PMSF and 20 units/ml aprotinin). The suspension was spun first at 10,000×g for 15 min and then at 100,000×g for 60 min. The supernatant was applied to an immobilized IFN-gamma column (7 mg per 1 ml of Affigel-10). Loading was at a flow rate of 0.2-0.5 ml/min. The column was then washed with PBS (50 ml) and the bound material was eluted with a solution of 50 mM Na$_2$CO$_3$ and 0.5M NaCl, pH 11. Fractions of 1 ml were collected and to immediately neutralized with 3M acetic acid. Each fraction was tested for its ability to bind [$^{125}$I]-IFN-gamma and for protein content. FIG. 4 shows the elution profile of the affinity column for WISH cells. Protein was determined with fluorescamine. Based on specific activity a purification factor of at least 2600 was obtained in one step.

EXAMPLE 3

Isolation of IFN-gamma receptors from human (KG-1) cells

Human KG-1 cells were grown in minimal essential medium (alpha-modification) supplemented with 10% foetal bovine serum and glutamine 2 mM. Cells were washed with phosphate buffered saline (PBS). 1-10×10$^{10}$ cells were solubilized in a solubilization buffer (final concentrations: 10 mM Hepes, pH 7.4, 1-2% Triton X-100, 1 mM PMSF and 20 units/ml aprotinin). The suspension was spun first at 10,000×g for 15 min and then at 100,000×g for 60 min. The supernatant was applied to an immobilized IFN-gamma column (7 mg per 1 ml of Affigel-10). Loading was at a flow rate of 0.2-0.5 ml/min. The column was then washed with PBS (50 ml) and the bound material was eluted with an appropriate buffer. Fractions of 1 ml were collected and immediately neutralized. Each fraction was tested for its ability to bind [$^{125}$I]-IFN-gamma and for protein content. Based on specific activity a purification factor of at least 1500 was obtained in one step.

EXAMPLE 4

Isolation of IFN-gamma receptors from human (Daudi) cells

Human Daudi cells were grown in RPMI-1640 medium supplemented with 10% foetal bovine serum and glutamine 2 mM. Cells were washed with phosphate buffered salim (PBS). $1-10\times10^{10}$ cells were solubilized in a solubilization buffer (final concentrations: 10 mM Hepes, pH 7.4, 1-2% Triton X-100, 1 mM PMSF and 20 units/ml aprotinin). The suspension was spun first at $10,000\times g$ for 15 min and then at $100,000\times g$ for 60 min. The supernatant was applied to an immobilized IFN-gamma column (7 mg per 1 ml of Affigel-10). Loading was at a flow rate of 0.2-0.5 ml/min. The column was then washed with PBS (50 ml) and the bound material was eluted with an appropriate buffer. Fractions of 1 ml were collected and to immediately neutralized. Each fraction was tested for its ability to bind $^{125}$I-IFN-gamma and for protein content. Protein was determined with fluorescamine. Based on specific activity a purification factor of at least 1000 was obtained in one step.

EXAMPLE 5

Binding of [$^{125}$I]-IFN-gamma and competition with cold ligand

Aliquots of various fractions from the affinity column of WISH cells containing 200 ng protein, mixed with [$^{125}$I]-IFN-gamma (130 1 units) either with or without unlabeled IFN-gamma (130,000 units). After incubation at 4° C. for 2 hr, gamma-globulin was added as a carrier and the proteins were precipitated by polyethelene glycol (PEG) (8000 M.W.). The mixture was filtered on a millipore (HAWP, 0.45u) membrane and membrane bound radioactivity determined. Background counts were determined in a similar reaction mixture but in the absence of soluble receptor. Table 1 shows that the binding of [$^{125}$I]-IFN-gamma to the protein in the elution fractions was completely displaced by cold ligands, indicating specificity in the binding. The background represented less than 20% of the total binding in the elution fraction and was substracted from all readings.

EXAMPLE 6

Saturation binding sites

Aliquots of elution fraction No. 6 (from example 2) containing 200 ng protein were mixed with increasing concentrations of [$^{125}$I]-IFN-gamma (5-6000 units/ml). The protein was precipitated and filtered, as explained previously.

Figure 5:
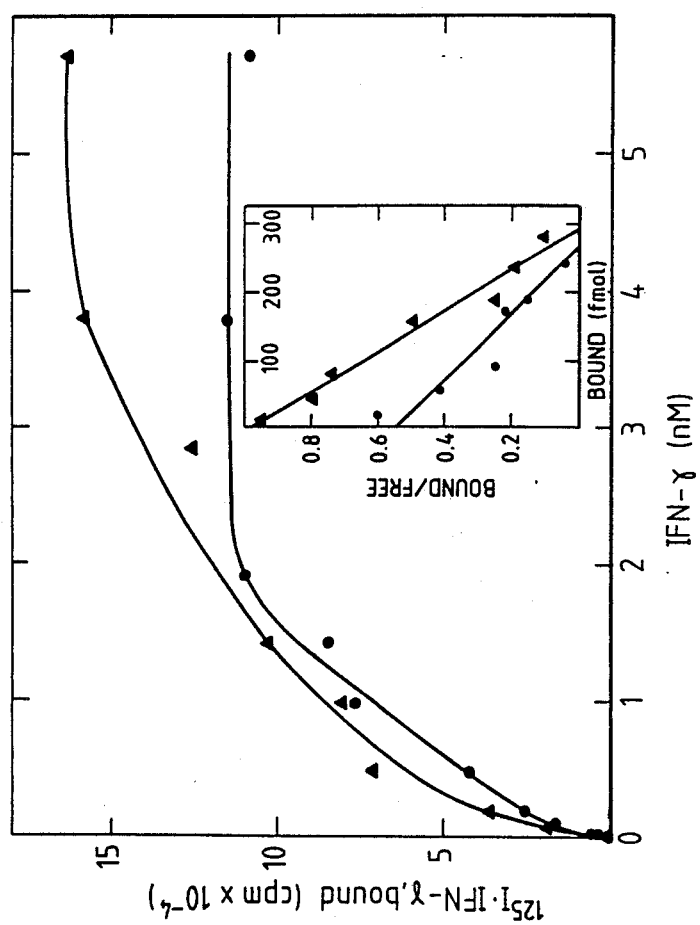
FIG. 5: Binding of [$^{125}$I]-IFN-gamma to elution fraction No. 6 (FIG. 4). Protein (200 ng) was incubated with increasing concentrations of [$^{125}$I]-IFN-gamma at 4° C. ( —▲— ) and at 37° C. ( —●— ). Free-radioactivity was separated from protein-bound radioactivity as described. Inset: Scatchard plots of the binding data.

FIG. 5 shows that [$^{125}$I]-IFN-gamma binds to the receptor in a saturable manner both at 4° C. and at 37° C. Scatchard analysis of the saturation curves show linear plots at both temperatures. The Kd at 4° C. was found to be $4.8\times10^{-10}$M and $2.95\times10^{-10}$M at 37° C. These values are in the same order of magnitude as those reported for intact cells.

EXAMPLE 7

Analysis of the purified receptor from WISH cells by crosslinking and immunoprecipitation Aliquots of various fractions of the affinity column of Example 2 were mixed with [$^{125}$I]-IFN-gamma in a final volume of 60 ul. Di-N-hydroxysuccinimidyl suberate (DSS) was added, and after incubation rabbit anti-IFN-gamma serum was added. The complex was precipitated by Protein-A Sepharose. Analysis of the samples was done by SDS-PAGE (7.5%), followed by autoradiography. FIG. 6 shows a complex of M.W. 115,000 as well as higher molecular weight bands obtained in the elution fractions. To further confirm the specificity of the immunoprecipitation a competition with either IFN-gamma (0, 10 or 1000-fold molar excess) or IFN-alpha (1000-fold molar excess) was performed. Specific inhibition of the immunoprecipitation was seen only by IFN-gamma (FIG. 6).

EXAMPLE 8

Immunization of mice

The partially purified preparations of interferon gamma receptors from the various cell lines were used as antigens to immunize female BALB/c mice. Mice were initially injected subcutaneously with 5 μg of a receptor preparation emulsified in complete Freunds adjuvant. Thirty days later the mice were injected subcutaneously with 5 μg receptor preparations. Injections were repeated three more times at 1 week intervals. The development of antibody level was followed by the ability of the mouse serum to inhibit the antiviral activity of IFN-gammma in human WISH cells and by its ability to inhibit the binding of [$^{125}$I]-interferon-gamma to KG-1 and to Daudi cells. In another experiment mice were injected subcutaneously with minced polyacrylamide gel containing the 95,000 band protein (2 μg) emulsified in complete Freund's adjuvant. Thirty days later the mice were injected subcutaneously with minced polyacrylamide gel containing the 95,000 band protein (2 μg). Infections were repeated three more times at 1 week intervals and the development of antibody level was followed by the ability of the mouse serum to inhibit the antiviral activity of IFN-gamma in human WISH cells.

EXAMPLE 9

Pharmaceutical Compositions

The compounds of the present invention can be formulated according to known methods to prepare pharmaceutically useful compositions, whereby either the purified receptor or the antibody product hereof or the F(ab') fragment of the antibody or inteferon gamma are combined in a mixture with a pharmaceutically acceptable carrier vehicle. Suitable vehicles and their formulation are described in Remington's *Pharmaceutical Sciences* by E. W. Martin. Such compositions will contain an effective amount of active substance hereof together with a suitable amount of vehicle in order to prepare pharmaceutically acceptable compositions suitable for effective administration to the host.

EXAMPLE 10

Parenteral Administration

The antibody or the purified receptor, both or mixed with interferon gamma may be parenterally administered to subjects requiring immunosuppressive or immunoregulatory treatment. Dosage and dose rate may parallel that currently in use in clinical investigations of other antibodies e.g. about 0.1-100 mg or even significantly elevated for greater effect.

As one example of an appropriate dosage form for essentially homogenous antibody in parenteral from applicable herein, 6 g of antibody may be dissolved in 250 ml serum albumin (human)-USP, the solution passed through a bacteriological filter and the filtered solution aseptically subdivided into 100 vials, each containing 60 mg pure antibody suitable for parenteral administration. The vials are preferably lyophilized and reconstituted with sterile water prior to use.

TABLE 1

Binding of $^{125}$I-IFN-γ and Competition with Cold Ligand

| Sample | Total Binding[a] cpm/200 ng | Specific Binding[b] (%) |
| --- | --- | --- |
| Load | 0 | 0 |
| Effluent | 0 | 0 |
| Wash 2 | 0 | 0 |
| Elution 1 | 47,200 | 100 |
| Elution 2 | 48,000 | 100 |
| Elution 3 | 47,000 | 100 |
| Elution 4 | 49,000 | 100 |

[a] Background (10,200 cpm) was substracted. Input: 268,000 cpm (130 units).
[b] Binding of $^{125}$I-IFN-γ in the presence of 1000-fold excess of cold IFN-γ

We claim:

1. A human gamma inteferon-specific receptor protein in a soluble and at least partially purified form, said protein not being an immunoglobulin.

2. The receptor protein of claim 1, which is a receptor protein of WISH, Hela and FS-11 cells having an approximate molecular weight of 90,000–105,000 dalton.

3. The receptor protein of claim 1, which is a receptor protein of monocytes and KG-1 cells having an approximate molecular weight of 140,000 dalton.

4. The receptor protein of claim 1, which is a receptor protein of Daudi lymphoblastoid cells having an approximate molecular weight of 95,000–115,000 dalton.

5. An antibody against the protein of claim 1.

6. An antibody against the protein of claim 2.

7. An antibody against the protein of claim 3.

8. An antibody against the protein of claim 4.

9. A composition comprising interferon gamma and the antibody of claim 1.

10. The composition of claim 9 comprising antibodies against at least one of the human interferon gamma receptors, but lacking an antibody against at least one other human interferon gamma receptor.

11. The composition of claim 10, lacking an antibody against the receptor protein of claim 2.

12. The composition of claim 10, lacking an antibody against the receptor protein of claim 3.

13. The composition of claim 10, lacking an antibody against the receptor protein of claim 4.

14. A composition comprising antibodies against at least one of the human interferon gamma receptors, but lacking an antibody against at least one other human interferon gamma receptors.

15. A composition comprising human interferon gamma and soluble receptor of claim 1 for controlling the therapeutical effect of human interferon gamma.

16. The composition comprising human interferon gamma and soluble receptor of claim 2 for controlling the therapeutical effect of human interferon gamma.

17. The composition comprising human interferon gamma and soluble receptor of claim 3 for controlling the therapeutical effect of human interferon gamma.

18. The composition comprising human interferon gamma and soluble receptor of claim 4 for controlling the therapeutical effect of human interferon gamma.

19. A human interferon gamma-specific receptor protein in substantially pure form.

20. The receptor protein of claim 19, further characterized as a receptor protein of WISH, Hela and FS-11 cells having an approximate molecular weight of 90,000–115,000 daltons.

21. The receptor protein of claim 19, further characterized as a receptor protein of monocytes and KG-1 cells having an approximate molecular weight of 140,000 daltons.

22. The receptor protein of claim 19, further characterized as a receptor protein of Daudi lymphoblastoid cells having an approximate molecular weight of 95,000–115,000 daltons.

* * * * *

UNITED STATES PATENT AND TRADEMARK OFFICE
CERTIFICATE OF CORRECTION

PATENT NO. : 4,897,264
DATED : January 30, 1990
INVENTOR(S) : NOVICK et al.

It is certified that error appears in the above-identified patent and that said Letters Patent is hereby corrected as shown below:

Column 9:

Claim No. 9, line 2    Delete "the", insert therefor -- an --

After "antibody", insert -- against the protein --

Signed and Sealed this

Third Day of November, 1992

Attest:

DOUGLAS B. COMER

Attesting Officer    Acting Commissioner of Patents and Trademarks